US00PP16018P2

(12) United States Plant Patent

Takeshita et al.

(10) Patent No.: US PP16,018 P2

(45) Date of Patent: Oct. 4, 2005

(54) *CALIBRACHOA* PLANT NAMED '01C-J-4'

(50) Latin Name: ***Calibrachoa* sp.**
Varietal Denomination: 01C-J-4

(75) Inventors: Daigaku Takeshita, Utsunomiya (JP); Saori Yamada, Ujiie-machi (JP); Yasuo Akiyama, Kazo (JP); Ayumi Yoma, Kaminokawa-machi (JP)

(73) Assignees: Kirin Brewery Company, LTD, Tokyo (JP); Tokith Seed Company, LTD, Saitama-ken (JP)

( * ) Notice: Subject to any disclaimer, the term of this patent is extended or adjusted under 35 U.S.C. 154(b) by 25 days.

(21) Appl. No.: 10/919,013

(22) Filed: Aug. 16, 2004

(51) Int. Cl.[7] ..... A01H 5/00

(52) U.S. Cl. ..... Plt./263

(58) Field of Search ..... Plt./263

*Primary Examiner*—Anne Marie Grunberg
(74) *Attorney, Agent, or Firm*—C. A. Whealy

(57) ABSTRACT

A new and distinct cultivar of *Calibrachoa* plant named '01C-J-4', characterized by its semi-prostrate, low mounding and outwardly spreading plant habit; freely branching growth habit; freely flowering habit; golden yellow-colored flowers with red-colored speckling and rust-colored venation; and good weather tolerance.

2 Drawing Sheets

Botanical classification/cultivar designation: *Calibrachoa* sp. cultivar 01C-J-4.

BACKGROUND OF THE INVENTION

The present Invention relates to a new and distinct cultivar of *Calibrachoa* plant, botanically known as *Calibrachoa* sp., and hereinafter referred to by the name '01C-J-4'.

The new *Calibrachoa* is a product of a planned breeding program conducted by the Inventors in Tochigi-ken, Japan. The objective of the breeding program is to create new early-flowering *Calibrachoa* cultivars that have stronger growth habit and attractive flower coloration.

The new *Calibrachoa* originated from a cross-pollination made by the Inventors in the Autumn of 2000, in Tochigi-ken, Japan, of the *Calibrachoa* cultivar Sunbelki, disclosed in U.S. Plant Pat. No. 11,558, as the female, or seed, parent with a proprietary *Calibrachoa* selection identified as code number 99-2-3, not patented, as the male, or pollen, parent. The new *Calibrachoa* was discovered and selected by the Inventors as a single flowering plant within the progeny of the stated cross-pollination grown in a controlled environment in Tochigi-ken, Japan, on Jun. 10, 2001. The selection of this plant was based on its strong plant growth habit and attractive flower coloration.

Asexual reproduction of the new cultivar by terminal cuttings in a controlled environment in Tochigi-ken, Japan, since Aug. 10, 2001, has shown that the unique features of this new *Calibrachoa* are stable and reproduced true to type in successive generations.

SUMMARY OF THE INVENTION

Plants of the cultivar 01C-J-4 have not been observed under all possible environmental conditions. The phenotype may vary somewhat with variations in environment such as temperature and light intensity without, however, any variance in genotype.

The following traits have been repeatedly observed and are determined to be the unique characteristics of '01C-J-4'.

These characteristics in combination distinguish '01C-J-4' as a new and distinct cultivar of *Calibrachoa:*

1. Semi-prostrate, low mounding and outwardly spreading plant habit.
2. Freely branching growth habit.
3. Freely flowering habit.
4. Golden yellow-colored flowers with red-colored speckling and rust-colored venation.
5. Good weather tolerance; tolerant to wind, rain, and low and high temperatures.

Plants of the new *Calibrachoa* are most similar to plants of the female parent, the cultivar Sunbelki. In side-by-side comparisons conducted by the Inventors in Tochigi-ken, Japan, plants of the new *Calibrachoa* differed from plants of the cultivar Sunbelki in the flowering characteristics:

1. Plants of the new *Calibrachoa* were not as prostrate in plant habit as plants of the cultivar Sunbelki.
2. Plants of the new *Calibrachoa* had smaller flowers than plants of the cultivar Sunbelki.
3. Plants of the new *Calibrachoa* flowered later than plants of the cultivar Sunbelki.
4. Plants of the new *Calibrachoa* and the cultivar Sunbelki differed in flower coloration as plants of the cultivar Sunbelki had light yellow-colored flowers.

Plants of the new *Calibrachoa* can also be compared to plants of the male parent selection. In side-by-side comparisons conducted by the Inventors in Tochigi-ken, Japan, plants of the new *Calibrachoa* differed from plants of the male parent selection in the flowering characteristics:

1. Plants of the new *Calibrachoa* were more freely flowering than plants of the male parent selection.
2. Plants of the new *Calibrachoa* and the male parent selection differed in flower coloration as plants of the male parent selection had dark yellow-colored flowers.

Compared to plants of the cultivar 01C-J-6, disclosed in a U.S. Plant patent application Ser. No. 10/919,012, plants of the new *Calibrachoa* flower later and differ in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new *Calibrachoa.*

The photograph on the first sheet comprises a side perspective view of a typical flowering plant of '01C-J-4'.

The photograph on the second sheet is a close-up view of typical flowers of '01C-J-4'.

DETAILED BOTANICAL DESCRIPTION

In the following description, color references are made to The Royal Horticultural Society Colour Chart, 1995 Edition, except where general terms of ordinary dictionary significance are used. Plants grown in one-gallon containers were used for the aforementioned photographs and the following description. Plants were grown under conditions which closely approximate commercial production conditions during the spring in Santa Paula, Calif. in a polyethylene-covered greenhouse. Plants were about five months old when the photographs and description were taken. During the production period, day temperatures ranged from 16 to 29° C., night temperatures ranged from 4 to 13° C., and maximum light levels ranged from 3,000 to 6,000 foot-candles.

Botanical classification: *Calibrachoa* sp. cultivar 01C-J-4.

Parentage:

*Female, or seed, parent.*—*Calibrachoa* sp. cultivar Sunbelki, disclosed in U.S. Plant Pat. No. 11,558.

*Male, or pollen, parent.*—Proprietary selection of *Calibrachoa* sp. identified as code number. 99-2-3, not patented.

Propagation:

*Type cutting.*—Terminal vegetative cuttings.

*Time to initiate roots.*—Summer: About 5 days at 25° C. Winter: About 8 days at 20° C.

*Time to produce a rooted young plant.*—Summer: About three weeks at 25° C. Winter: About four weeks at 22° C.

*Root description.*—Fine, fibrous, and white in color.

*Rooting habit.*—Freely branching; dense.

Plant description:

*Form.*—Annual flowering plant; semi-prostrate, low mounding and outwardly spreading plant habit; dense and bushy appearance.

*Plant height* (*from soil level to top of plant plane*).—About 25 cm.

*Plant diameter* (*area of spread*).—About 34 cm.

*Growth rate.*—Moderate to rapid; vigorous.

*Branching habit.*—Freely basal branching, about six to seven basal branches per plant; lateral branches develop at potentially every node; pinching is typically not required.

*Lateral branch description.*—Length: About 45 cm. Diameter: About 4.5 mm. Internode length: About 1 cm. Orientation: Initially upright, then nearly horizontal to trailing. Texture: Pubescent; short, fine hairs. Strength: Strong, but flexible. Color: 144B overlain with 187A.

*Foliage description.*—Arrangement: Alternate before flowering; when flowering, opposite; simple. Length: About 2.7 cm. Width: About 9 mm. Shape: Elliptic. Apex: Broadly acute. Base: Attenuate. Margin: Entire. Texture, upper and lower surfaces: Slightly glandular and slightly pubescent. Venation pattern: Pinnate; arcuate. Color: Developing foliage, upper and lower surfaces: 144A. Fully expanded foliage, upper surface: 146A. Fully expanded foliage, lower surface: 146B. Venation, upper surface: 146A. Venation, lower surface: 146D. Petiole length: About 7 mm. Petiole diameter: About 1.5 mm. Petiole texture, upper and lower surfaces: Slightly pubescent. Petiole color, upper and lower surfaces: 144A.

Flower description:

*Flower type and habit.*—Flowers face upright or outwardly; flowers solitary and axillary; salverform. Freely flowering habit, about 24 to 30 flowers per lateral stem. Flowers persistent.

*Fragrance.*—None detected.

*Natural flowering season.*—Spring until frost in the autumn; flowering continuous during this period.

*Time to flower.*—Plants begin flowering about 45 days after planting.

*Flower longevity on the plant.*—About one week.

*Flower size.*—Diameter: About 3 cm by 3.2 cm. Depth: About 2.8 cm. Tube length: About 1.8 cm. Throat diameter: About 7 mm. Tube diameter, proximal: About 2.5 mm.

*Flower buds* (*at stage of showing color*).—Length: About 2.3 cm. Diameter: About 5 mm. Shape: Elongate. Color: 51A.

*Corolla.*—Arrangement/appearance: Single whorl of five petals, fused into flared trumpet. Petal length from throat: About 1.3 cm. Petal width: About 1.6 cm. Petal shape: Fan-shaped to obovate. Petal apex: Rounded to obtuse. Petal margin: Entire. Petal texture, upper and lower surfaces: Smooth, glabrous; velvety. Color: Petal, when opening, upper surface: 20C; speckling, 44C; venation, 173B. Petal, when opening, lower surface: 71D; venation, 183D. Petal, fully opened flower, upper surface: 20C; speckling, 44C to 44D; venation, 173B. Main color becoming closer to 19B and speckling, 39C, with development. Petal, fully opened flower, lower surface: 63B; venation, 183D. Flower throat (inside): 14A; venation, 174B. Flower tube (outside): 10B; venation, 176A.

*Sepals.*—Arrangement/appearance: Single whorl of five sepals fused at base; star-shaped. Length: About 1.6 cm. Width: About 2.5 mm. Shape: Narrowly lanceolate. Apex: Acute. Margin: Entire. Texture, upper and lower surfaces: Smooth, glabrous. Color: Developing and fully expanded, upper surface: 144A. Developing and fully expanded, lower surface: 146B.

*Peduncles.*—Length: About 1 cm. Width: About 1 mm. Strength: Moderately strong. Angle: About 45 to 60° from stem. Texture: Finely pubescent. Color: 144A.

*Reproductive organs.*—Stamens: Quantity per flower: Typically five. Anther shape: Oval. Anther length: Less than 1 mm. Anther color: 11A. Pollen amount: Scarce. Pollen color: 12A. Pistils: Quantity per flower: One. Pistil length: About 1.2 cm. Stigma shape: Oval. Stigma color: 144A. Style length: About 9 mm. Style color: 145C. Ovary color: 145A.

*Seed/fruit.*—Seed and fruit production has not been observed.

Disease/pest resistance: Plants of the new *Calibrachoa* have not been noted to be resistant to pathogens and pests common to *Calibrachoa*.

Weather/temperature tolerance: Plants of the new *Calibrachoa* are tolerant to rain and wind and have been observed to tolerate temperatures from 3 to 35° C.

It is claimed:

1. A new and distinct cultivar of *Calibrachoa* plant named '01C-J-4' as illustrated and described.

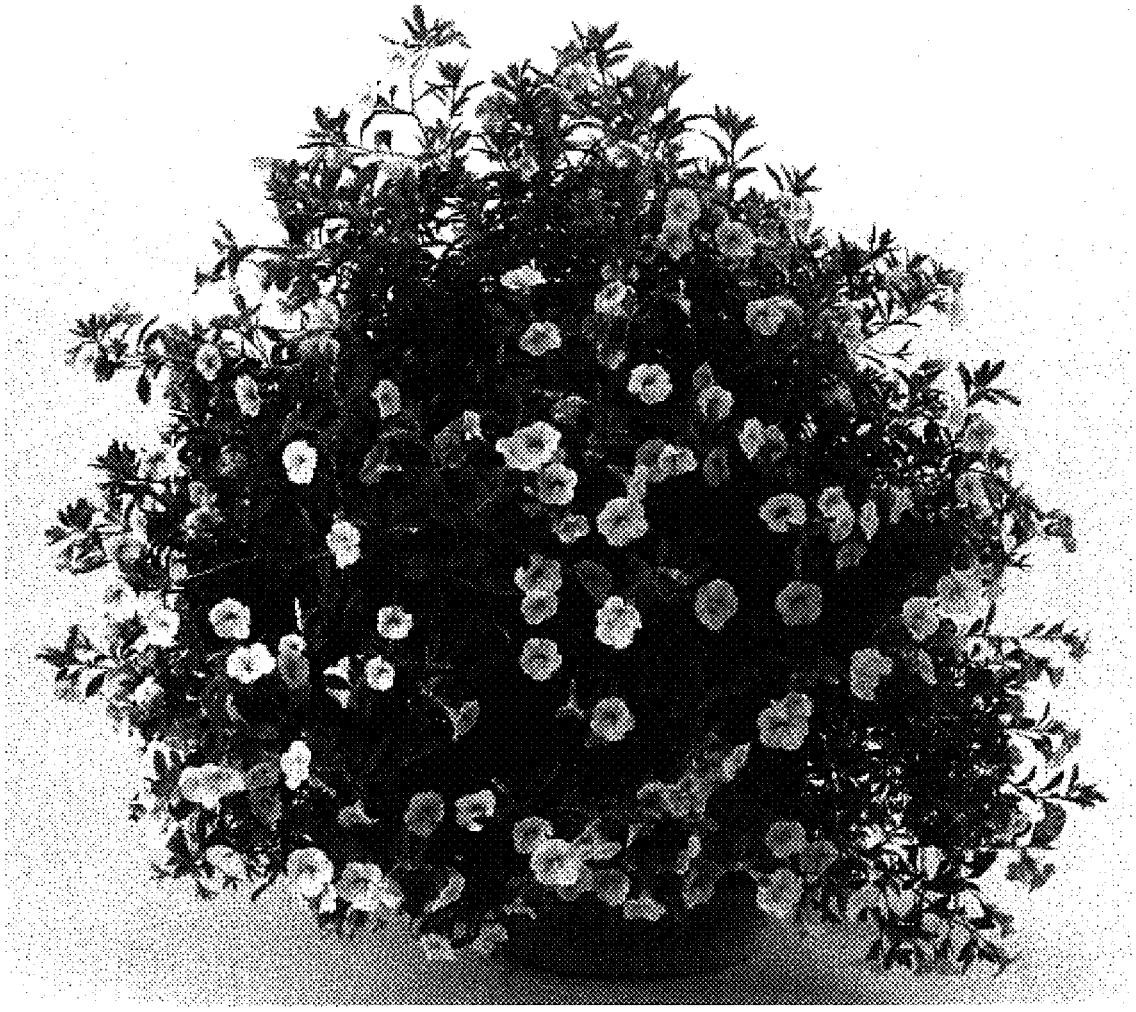

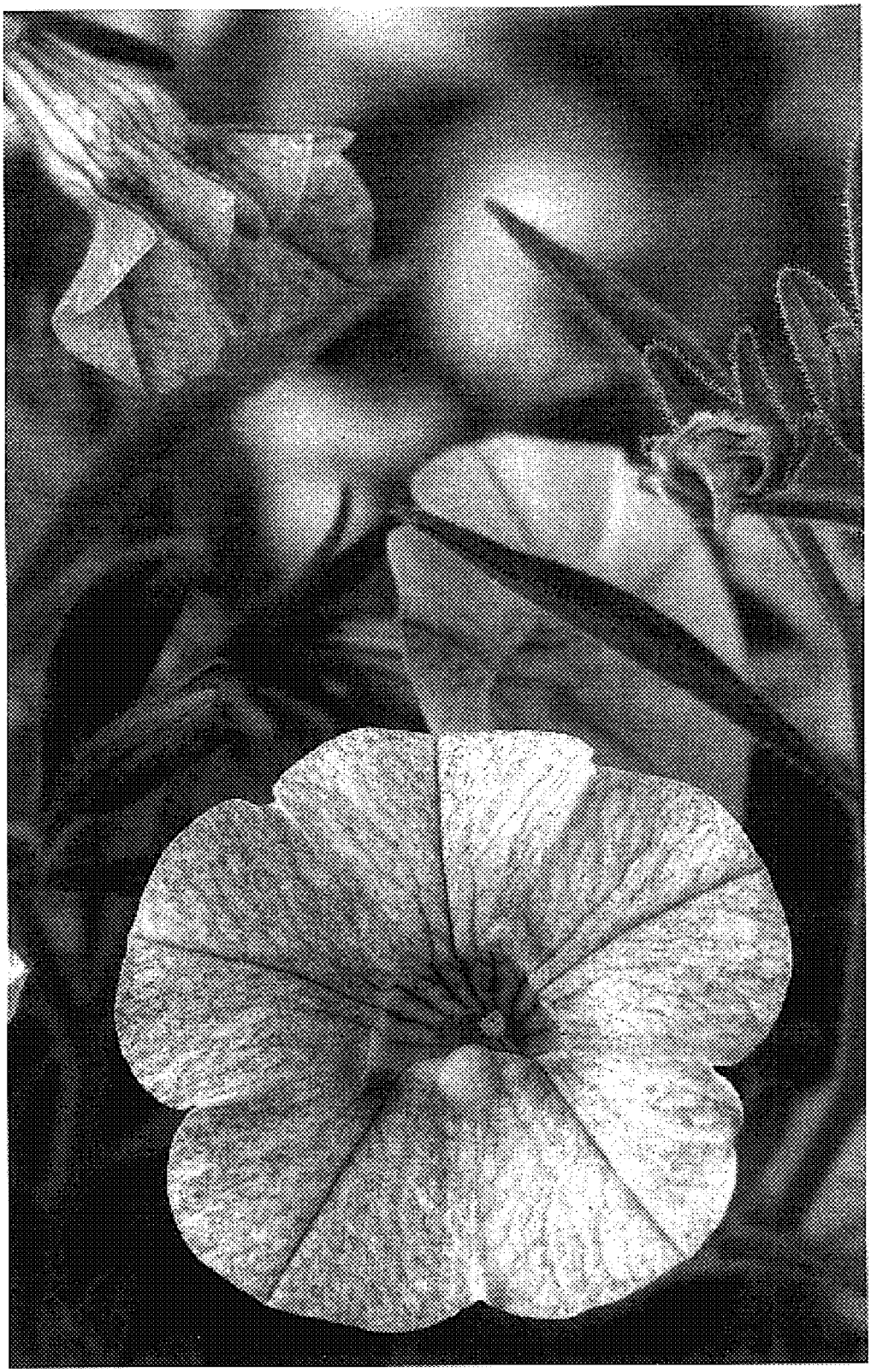

* * * * *